(12) United States Patent
Haas et al.

(10) Patent No.: US 8,458,841 B2
(45) Date of Patent: Jun. 11, 2013

(54) BRUSH HEAD FOR A TOOTHBRUSH

(75) Inventors: Martin Haas, Frankfurt am Main (DE);
Ivo Kunath, Kronberg/Taunus (DE);
Armin Schwarz-Hartmann,
Wendelsheim (DE)

(73) Assignee: Braun GmbH, Kronberg (DE)

( * ) Notice: Subject to any disclaimer, the term of this patent is extended or adjusted under 35 U.S.C. 154(b) by 539 days.

(21) Appl. No.: 12/663,913

(22) PCT Filed: Jun. 5, 2008

(86) PCT No.: PCT/EP2008/004476
§ 371 (c)(1),
(2), (4) Date: Jun. 29, 2010

(87) PCT Pub. No.: WO2008/155025
PCT Pub. Date: Dec. 24, 2008

(65) Prior Publication Data
US 2010/0269279 A1 Oct. 28, 2010

(30) Foreign Application Priority Data

Jun. 20, 2007 (DE) .......................... 10 2007 028 184

(51) Int. Cl.
*A46B 13/04* (2006.01)
*A61C 17/28* (2006.01)
*A61C 17/36* (2006.01)

(52) U.S. Cl.
USPC .................................. 15/29; 433/80; 601/162

(58) Field of Classification Search
USPC ................. 15/29, 24, 22.1; 601/17, 112, 114, 601/160, 161, 162, 165; 401/286, 282, 271, 401/270; 433/80, 216
See application file for complete search history.

(56) References Cited

U.S. PATENT DOCUMENTS

| 1,327,757 A | 1/1920 | Eggers |
| 1,664,369 A | 3/1928 | Maurer |

(Continued)

FOREIGN PATENT DOCUMENTS

| CA | 1151 821 | 8/1983 |
| DE | 238191 | 11/1910 |

(Continued)

OTHER PUBLICATIONS

Bushing from The American Heritage Dictionary of the English Language, 2007.*

(Continued)

*Primary Examiner* — Mark Spisich
*Assistant Examiner* — Andrew A Horton
(74) *Attorney, Agent, or Firm* — John P. Colbert; George H. Leal

(57) ABSTRACT

The invention relates to a brush head for a toothbrush. The brush head has a brush disc (3) mounted in a rotatable fashion on a brush body (2) and a channel (7) with an opening for the application of a cleaning product and a composite part (6) that serves as a valve (12) for opening the channel (7) and as a rotational bearing for the brush disc (3). The composite part (6) comprises a tube (8) made of hard material on the one end thereof and is connected to the channel (7) there. The valve (12), which is made of an elastic material, is disposed on the other end of the composite part (6). The tube (8) of the compound part (6) is connected to the brush body (2) in a stationary fashion, for example, pressed into the brush body (2). The brush disc (3) is mounted in a rotatable fashion on the tube (8). The valve (12) is preferably designed as a slotted valve with a slot (13).

5 Claims, 2 Drawing Sheets

U.S. PATENT DOCUMENTS

Figure 1:
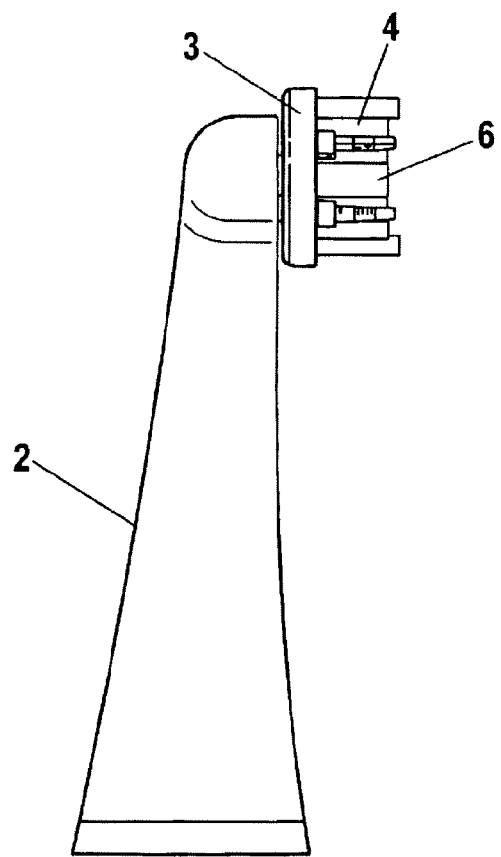

| | | |
|---|---|---|
| 2,303,667 A | 12/1942 | Taborski |
| 2,661,537 A | 12/1953 | Angell |
| 2,691,553 A | 10/1954 | Pettigrew |
| 2,696,049 A | 12/1954 | Black |
| 2,757,688 A | 8/1956 | Meyer-Saladin |
| 2,759,266 A | 8/1956 | Cassani |
| 2,813,529 A | 11/1957 | Ikse |
| 3,134,127 A | 5/1964 | Klein |
| 3,164,153 A | 1/1965 | Zorzi |
| 3,195,537 A | 7/1965 | Blasi |
| 3,234,953 A | 2/1966 | Moynihan |
| 2,743,042 A | 4/1966 | Burgin |
| 3,400,996 A | 9/1968 | Macrum |
| RE26,589 E | 5/1969 | Murov |
| D214,829 S | 8/1969 | Muscatiello |
| 3,496,933 A | 2/1970 | Lloyd |
| 3,536,065 A | 10/1970 | Moret |
| 3,578,887 A | 5/1971 | Turolla |
| 3,593,707 A | 7/1971 | Pifer |
| 3,608,548 A | 9/1971 | Lewis |
| 3,610,514 A | 10/1971 | Samsing |
| 3,628,875 A | 12/1971 | Wild |
| 3,771,186 A | 11/1973 | Moret |
| 3,823,710 A | 7/1974 | Borden |
| 3,864,047 A | 2/1975 | Sherrod |
| 3,870,039 A | 3/1975 | Moret |
| 3,878,577 A | 4/1975 | Jousson |
| 3,903,888 A | 9/1975 | Minnesota |
| 3,910,706 A | 10/1975 | Del Bon |
| 3,971,136 A | 7/1976 | Madsen |
| 3,972,133 A | 8/1976 | Black |
| 4,146,020 A | 3/1979 | Moret |
| 4,155,663 A | 5/1979 | Cerquozzi |
| 4,174,571 A | 11/1979 | Gallant |
| 4,178,975 A | 12/1979 | Crespi |
| 4,201,200 A | 5/1980 | Hubner |
| 4,214,871 A | 7/1980 | Arnold |
| 4,236,889 A | 12/1980 | Wright |
| 4,322,207 A | 3/1982 | Madsen |
| 4,412,402 A | 11/1983 | Gallant |
| 4,422,450 A | 12/1983 | Rusteberg |
| 4,429,434 A | 2/1984 | Sung Shan |
| 4,438,810 A | 3/1984 | Atkinson |
| 4,467,822 A | 8/1984 | Blackwell |
| 4,518,557 A | 5/1985 | Wecker |
| 4,522,597 A | 6/1985 | Gallant |
| 4,528,180 A | 7/1985 | Schaeffer |
| 4,534,340 A | 8/1985 | Kerr |
| 4,540,365 A | 9/1985 | Nelson |
| 4,583,563 A | 4/1986 | Turner |
| 4,595,365 A | 6/1986 | Edel |
| 4,619,009 A | 10/1986 | Rosenstatter |
| 4,627,977 A | 12/1986 | Gaffaretal |
| 4,666,708 A | 5/1987 | Goldemberg et al. |
| 4,692,047 A | 9/1987 | Endo |
| 4,696,644 A | 9/1987 | Mizusawa |
| 4,735,200 A | 4/1988 | Westerman |
| 4,743,199 A | 5/1988 | Weber |
| 4,770,632 A | 9/1988 | Ryder |
| 4,776,794 A | 10/1988 | Meller |
| 4,818,191 A | 4/1989 | Schlake |
| 4,863,302 A | 9/1989 | Herzfeld |
| 4,903,688 A | 2/1990 | Bibby |
| 4,906,187 A | 3/1990 | Amadera |
| 4,941,459 A | 7/1990 | Mathur |
| 4,950,160 A | 8/1990 | Karst |
| 4,963,046 A | 10/1990 | Eguchi |
| 4,997,640 A | 3/1991 | Bird et al. |
| 5,055,043 A | 10/1991 | Weiss |
| 5,062,795 A | 11/1991 | Woog |
| 5,066,155 A | 11/1991 | English |
| 5,098,291 A | 3/1992 | Curtis |
| 5,120,219 A | 6/1992 | De Farcy |
| 5,142,723 A | 9/1992 | Lustig |
| 5,147,203 A | 9/1992 | Seidenberg |
| 5,203,698 A | 4/1993 | Blake |
| 5,208,933 A | 5/1993 | Lustig |
| 5,219,274 A | 6/1993 | Pawlowski |
| 5,286,192 A | 2/1994 | Dixon |
| 5,301,381 A | 4/1994 | Klupt |
| 5,321,866 A | 6/1994 | Klupt |
| 5,332,370 A | 7/1994 | Nakayama |
| 5,338,124 A | 8/1994 | Spicer |
| 5,344,317 A | 9/1994 | Pacher |
| 5,346,324 A | 9/1994 | Kuo |
| 5,387,182 A | 2/1995 | Otani |
| 5,393,153 A | 2/1995 | Bouthillier |
| 2,709,546 A | 5/1995 | Shore |
| 5,454,896 A | 10/1995 | Harding et al. |
| 5,474,544 A | 12/1995 | Lynn |
| 5,484,281 A | 1/1996 | Renow et al. |
| 5,492,147 A | 2/1996 | Challender et al. |
| 5,501,426 A | 3/1996 | Atkinson et al. |
| 5,503,553 A | 4/1996 | Hines |
| 5,509,433 A | 4/1996 | Paradis |
| 5,524,312 A | 6/1996 | Tan et al. |
| 5,530,215 A | 6/1996 | Couvreur |
| 5,540,358 A | 7/1996 | Wiles et al. |
| 5,560,905 A | 10/1996 | Lukacovic |
| 5,573,398 A | 11/1996 | Towle |
| 5,578,059 A | 11/1996 | Patzer |
| 5,593,304 A | 1/1997 | Ram |
| 5,600,933 A | 2/1997 | Wiles et al. |
| 5,653,591 A | 8/1997 | Loge |
| 5,690,017 A | 11/1997 | Riedlinger |
| 5,699,821 A | 12/1997 | Paradis |
| 5,702,033 A | 12/1997 | Beaver |
| 5,711,488 A | 1/1998 | Lund |
| 5,746,595 A | 5/1998 | Ford |
| 5,755,572 A | 5/1998 | Itai et al. |
| 5,769,585 A | 6/1998 | Pudolsky |
| 5,806,831 A | 9/1998 | Paradis |
| 5,820,373 A | 10/1998 | Okano |
| 5,871,353 A | 2/1999 | Pierce et al. |
| 5,909,977 A | 6/1999 | Kuo |
| 5,918,995 A | 7/1999 | Puurunen |
| 5,921,692 A | 7/1999 | Weber |
| 5,974,613 A | 11/1999 | Herzog |
| 6,030,215 A | 2/2000 | Ellion |
| 6,039,301 A | 3/2000 | Westerhof |
| 6,039,302 A | 3/2000 | Cote et al. |
| 6,065,389 A | 5/2000 | Riedlinger |
| 6,068,011 A | 5/2000 | Paradis |
| 6,079,432 A | 6/2000 | Paradis |
| 6,106,288 A | 8/2000 | Brassil |
| 6,113,068 A | 9/2000 | Ryan |
| 6,164,967 A | 12/2000 | Sale |
| 6,189,859 B1 | 2/2001 | Rohrbough et al. |
| 6,217,327 B1 | 4/2001 | Bedi |
| 6,220,772 B1 | 4/2001 | Taylor |
| 6,221,341 B1 | 4/2001 | Montgomery |
| 6,233,733 B1 | 5/2001 | Karge |
| 6,241,412 B1 | 6/2001 | Spies et al. |
| 6,264,119 B1 | 7/2001 | Truong |
| 6,299,443 B1 | 10/2001 | Gerstner |
| 6,315,483 B1 | 11/2001 | Velliquette |
| 6,331,088 B2 | 12/2001 | Owens |
| 6,347,614 B1 | 2/2002 | Evers |
| 6,357,125 B1 | 3/2002 | Feldmann et al. |
| 6,371,674 B1 | 4/2002 | Lerner |
| 6,375,459 B1 | 4/2002 | Kamen |
| 6,402,410 B1 | 6/2002 | Hall et al. |
| 6,419,485 B1 | 7/2002 | Pond |
| 6,434,773 B1 | 8/2002 | Kuo |
| 6,457,476 B1 | 10/2002 | Elmer et al. |
| 6,536,979 B1 | 3/2003 | Kenny |
| 6,564,972 B2 | 5/2003 | Sawhney et al. |
| 6,574,820 B1 | 6/2003 | DePuydt et al. |
| 6,575,203 B2 | 6/2003 | Hall et al. |
| 6,602,701 B2 | 8/2003 | Ellion |
| 6,644,878 B2 | 11/2003 | Hall et al. |
| 6,648,641 B1 | 11/2003 | Viltro et al. |
| 6,681,803 B2 | 1/2004 | Taneya et al. |
| 6,696,047 B2 | 2/2004 | Scott et al. |
| 6,745,998 B2 | 6/2004 | Doyle |
| 6,766,549 B2 | 7/2004 | Klupt |
| 6,766,824 B2 | 7/2004 | Taylor |

| | | | |
|---|---|---|---|
| 6,808,161 B1 | 10/2004 | Hishikawa | |
| 6,808,331 B2 | 10/2004 | Hall | |
| 6,883,778 B1 | 4/2005 | Newton et al. | |
| 6,884,069 B2 | 4/2005 | Goldman | |
| 6,902,337 B1 | 6/2005 | Kuo | |
| 6,957,925 B1 | 10/2005 | Jacobs et al. | |
| 7,036,179 B1 | 5/2006 | Weihrauch | |
| 7,080,980 B2 | 7/2006 | Klupt | |
| 7,147,468 B2 | 12/2006 | Snyder et al. | |
| 7,161,489 B2 | 1/2007 | Sullivan | |
| 7,341,208 B2 | 3/2008 | Peters et al. | |
| 7,469,440 B2 | 12/2008 | Boland et al. | |
| 7,530,796 B2 | 5/2009 | Yu et al. | |
| 2001/0002228 A1 | 5/2001 | Owens | |
| 2002/0106336 A1 | 8/2002 | Glandorf et al. | |
| 2002/0108193 A1 | 8/2002 | Gruber | |
| 2002/0152565 A1* | 10/2002 | Klupt | 15/29 |
| 2003/0013603 A1 | 1/2003 | Goldman | |
| 2003/0027100 A1 | 2/2003 | Grant | |
| 2003/0033680 A1 | 2/2003 | Davies et al. | |
| 2003/0053847 A1 | 3/2003 | Carlucci et al. | |
| 2003/0060743 A1 | 3/2003 | Chang | |
| 2003/0086745 A1 | 5/2003 | Micaletti | |
| 2003/0099502 A1 | 5/2003 | Lai | |
| 2003/0126705 A1 | 7/2003 | Hanlon | |
| 2003/0150472 A1 | 8/2003 | Johnson | |
| 2003/0152565 A1 | 8/2003 | Bartorelli | |
| 2003/0194678 A1 | 10/2003 | Viltro et al. | |
| 2003/0198503 A1 | 10/2003 | Gordon | |
| 2003/0198604 A1 | 10/2003 | Lawlor | |
| 2003/0211050 A1 | 11/2003 | Majeti et al. | |
| 2004/0047676 A1 | 3/2004 | Dumler | |
| 2004/0057773 A1 | 3/2004 | Gray | |
| 2004/0062591 A1 | 4/2004 | Hall et al. | |
| 2004/0126331 A1 | 7/2004 | Corcoran et al. | |
| 2004/0131560 A1 | 7/2004 | Corcoran et al. | |
| 2004/0141799 A1 | 7/2004 | Jackow | |
| 2004/0143917 A1 | 7/2004 | Ek | |
| 2004/0150258 A1 | 8/2004 | McCarthy | |
| 2004/0186444 A1* | 9/2004 | Daly et al. | 604/247 |
| 2004/0241109 A1 | 12/2004 | Parikh | |
| 2005/0000541 A1 | 1/2005 | Engel | |
| 2005/0004498 A1 | 1/2005 | Klupt | |
| 2005/0060822 A1 | 3/2005 | Chenvainu | |
| 2005/0158688 A1 | 7/2005 | Tarr | |
| 2005/0163727 A1 | 7/2005 | Doyle et al. | |
| 2005/0271531 A1 | 12/2005 | Christman et al. | |
| 2005/0272001 A1 | 12/2005 | Blain et al. | |
| 2005/0272002 A1* | 12/2005 | Chenvainu et al. | 433/80 |
| 2005/0281758 A1 | 12/2005 | Dodd | |
| 2006/0078844 A1 | 4/2006 | Goldman et al. | |
| 2006/0159509 A1 | 7/2006 | Grez et al. | |
| 2006/0188454 A1 | 8/2006 | Corcoran et al. | |
| 2006/0193792 A1 | 8/2006 | Corcoran et al. | |
| 2006/0240380 A1 | 10/2006 | Chenvainu et al. | |
| 2006/0289031 A1 | 12/2006 | Grez et al. | |
| 2007/0017582 A1 | 1/2007 | Chenvainu et al. | |
| 2007/0105065 A1 | 5/2007 | Snyder et al. | |
| 2007/0113903 A1 | 5/2007 | Black | |
| 2007/0212662 A1 | 9/2007 | Grez | |
| 2007/0254260 A1 | 11/2007 | Alden et al. | |
| 2007/0275347 A1 | 11/2007 | Gruber | |
| 2009/0017423 A1 | 1/2009 | Gottenbos et al. | |
| 2009/0070949 A1 | 3/2009 | Sagel | |
| 2009/0085515 A1 | 4/2009 | Bourilkov | |
| 2009/0191071 A1 | 7/2009 | Yu et al. | |

FOREIGN PATENT DOCUMENTS

| | | |
|---|---|---|
| DE | 2041495 | 4/1972 |
| DE | 2343421 | 3/1975 |
| DE | 2758182 | 7/1978 |
| DE | 2746453 A1 | 4/1979 |
| DE | 2746453 C2 | 4/1979 |
| DE | 2819404 | 8/1979 |
| DE | 3904139 | 8/1990 |
| DE | 9107226 | 10/1991 |
| DE | 29816089 | 1/1999 |
| DE | 10137879 | 2/2003 |
| DE | 20306197 | 7/2003 |
| DE | 102007025485.2 | 5/2007 |
| EP | 1107453 | 6/2001 |
| FR | 1193546 | 11/1959 |
| FR | 1491238 | 7/1967 |
| FR | 2 770 768 | 5/1999 |
| GB | 233018 | 4/1925 |
| GB | 762230 | 11/1956 |
| GB | 2019961 | 11/1979 |
| GB | 2 067 396 | 7/1981 |
| GB | 2087025 | 5/1982 |
| GB | 2343619 A | 5/2000 |
| GB | 2378894 | 2/2003 |
| JP | 63286147 | 11/1988 |
| JP | 9215524 | 8/1997 |
| JP | 10033571 | 4/1998 |
| TW | 512059 | 12/2002 |
| WO | WO 82/00576 | 3/1982 |
| WO | WO 94/08533 | 4/1994 |
| WO | WO 95/08934 A1 | 4/1995 |
| WO | WO 99/23975 | 5/1999 |
| WO | WO 00/45731 | 8/2000 |
| WO | WO 00/74592 | 12/2000 |
| WO | WO 01/03542 A2 | 1/2001 |
| WO | WO 03/005926 A2 | 1/2003 |
| WO | WO 03/063643 A1 | 8/2003 |
| WO | WO 2004/049968 | 6/2004 |
| WO | WO2006/067748 | 6/2006 |
| WO | WO2006/067760 | 6/2006 |
| WO | WO2007/010746 A1 | 1/2007 |
| WO | WO2008/145320 | 12/2008 |
| WO | WO2008/155025 | 12/2008 |

OTHER PUBLICATIONS

DWPI Accession No. 2003-240906 (Feb. 20, 2003).
DWPI Accession No. 2003-241468 (Feb. 26, 2003).
DWPI Accession No. 2003-277227 (Feb. 6, 2003).
DWPI Accession No. 2003-468010 (May 29, 2003).
DWPI Accession No. 2003-560479 (2003).
DWPI Accession No. 2003-567147 (2003).
DWPI Accession No. 2003-568454 (2003).
DWPI Accession No. 2003-575803 (2003).
DWPI Accession No. 2003-577960 (2003).
Office Action for U.S. Appl. No. 10/960,467 dated Sep. 26, 2007, P&G Case Z-3472, Goldman et al.
Office Action for U.S. Appl. No. 10/960,467 dated Feb. 18, 2009, P&G Case Z-3472, Goldman et al.
Office Action for U.S. Appl. No. 10/960,467 dated Jul. 17, 2009, P&G Case Z-3472, Goldman et al.
Office Action for U.S. Appl. No. 10/960,467 dated Feb. 4, 2010, P&G Case Z-3472, Goldman et al.
Office Action for U.S. Appl. No. 11/605,559 dated Apr. 8, 2010, P&G Case Z-3546M, Alden IV et al.
Office Action for U.S. Appl. No. 11/605,559 dated Sep. 14, 2010, P&G Case Z-3546M, Alden IV et al.
Office Action for U.S. Appl. No. 11/605,559 dated May 6, 2009, P&G Case Z-3546M, Alden IV et al.
Office Action for U.S. Appl. No. 11/605,559 dated Nov. 19, 2008, P&G Case Z-3546M, Alden IV et al.
Office Action for U.S. Appl. No. 11/114,987, dated Feb. 25, 2008, P&G Case Z-3519, Chenvainu et al.
Office Action for U.S. Appl. No. 11/114,987, dated Aug. 15, 2008, P&G Case Z-3519, Chenvainu et al.
Office Action for U.S. Appl. No. 11/114,987, dated Feb. 13, 2009, P&G Case Z-3519, Chenvainu et al.
Office Action for U.S. Appl. No. 11/114,987, dated Sep. 4, 2009, P&G Case Z-3519, Chenvainu et al.
Office Action for U.S. Appl. No. 11/114,987, dated Feb. 2, 2010, P&G Case Z-3519, Chenvainu et al.
Office Action for U.S. Appl. No. 11/114,987, dated May 10, 2010, P&G Case Z-3519, Chenvainu et al.
Office Action for U.S. Appl. No. 11/114,987, dated Aug. 24, 2010, P&G Case Z-3519, Chenvainu et al.
Office Action for U.S. Appl. No. 11/114,987, dated Mar. 25, 2011, P&G Case Z-3519, Chenvainu et al.

Office Action for U.S. Appl. No. 10/861,086, dated Aug. 14, 2008, P&G Case Z-3475, Blain et al.

Office Action for U.S. Appl. No. 10/861,086, dated Dec. 10, 2007, P&G Case Z-3475, Blain et al.

Office Action for U.S. Appl. No. 10/861,086, dated Jan. 8, 2007, P&G Case Z-3475, Blain et al.

Office Action for U.S. Appl. No. 10/861,086, dated Mar. 13, 2009, P&G Case Z-3508, Chenvainu et al.

Office Action for U.S. Appl. No. 10/861,086, dated Oct. 1, 2008, P&G Case Z-3508, Chenvainu et al.

Office Action for U.S. Appl. No. 10/861,086, dated Dec. 28, 2007, P&G Case Z-3508, Chenvainu et al.

PCT International Search Report dated Sep. 24, 2008 for Z-8013.

PCT International Search Report dated Feb. 13, 2006 for Z-3472.

PCT International Search Report received in connection with PCT/US2006/015392, mailed on Feb. 23, 2007 for Z-3519.

PCT International Search Report dated Jan. 12, 2006 for Z-3546.

* cited by examiner

BRUSH HEAD FOR A TOOTHBRUSH

The invention relates to a brush head for a toothbrush that has a brush disc mounted in a rotatable fashion on a brush body and an opening for the application of a cleaning product.

Manually operated toothbrushes and electrically driven toothbrushes are already known in which a care substance can be fed onto the brush head by a pump. The most comfortable solution for the user is when the care substance is discharged directly onto the brush head as well as when it is continuously fed onto the brush head while cleaning the teeth. Electric toothbrushes whose brush head has a movable brush disc must feed the care substance from a fixed throat onto the movable brush disc. This can lead, on the one hand, to difficulties with regard to the seal between the fixed and movable parts of the brush head and the movable mounting of the brush disc. On the other hand, measures must be taken in order to prevent the feeding channel for the care substance from drying out.

The object of the invention is therefore to create a simply constructed brush head that has a brush disc mounted in a rotatable fashion and a channel with an opening for the application of a care product while avoiding the aforementioned difficulties.

To achieve this object, the brush head has a composite part that has a sealing device on the one end thereof that is preferably made of an elastic material, and is designed, for example, as a slotted valve, and which is connected at its other end with a channel through which a care product can be fed. This end preferably consists of a tubular core made of a hard material that is suitable as a swivel for the brush disc.

Advantageous developments of the invention are indicated in the sub-claims.

The brush head can be part of an attachment brush that can be attached onto a handle part of a toothbrush or which can also be part of a toothbrush in which only the brush disc can be replaced. The composite part is connected to a brush body of the brush head, in which the channel is designed to convey the care product.

The brush head has been conceived for a toothbrush that has a reservoir for receiving liquid or paste-like products for treating the oral cavity. These substances can be for cleaning teeth as well as general products for cleaning and caring for the oral cavity, for example products for the prevention of cavities, treatment of gums and inflammations, reduction of bad breath, teeth bleaching or brightening, remineralization of tooth enamel, desensitizing sensitive teeth, or for other applications. These care products are fed to the brush disc through a channel and discharged via the valve. The care product can be filled in replaceable pouches or cartridges and stored in the hand piece. The care product is preferably conveyed via a pump that is either activated manually by the user or activated by an electrical drive mechanism.

In order to prevent the care product from drying out or to prevent contamination with bacteria from the oral cavity, there is a valve located on the outlet of the channel. This valve is part of a composite part that consists of two components. The component that protrudes above the brush disc is made of an elastic material. This material can come from the group of elastomers (e.g., rubber compounds, silicones, NBR or EPDM) or, in particular, thermoplastic elastomers (TPE). In order to attach the valve securely and seal it against the brush body, a hard substance is used as the second component. In one preferred embodiment, the elastic valve is made of rubber and the second component is made of steel; they are firmly connected to each other by a vulcanization process. The pull-off forces of the rubber from the steel can be set so high that the rubber will not detach from the steel, even under high stress; rather, it will tear. The same result can be achieved with a composite part that is produced in a two-component injection-mold process and made of a hard plastic and a TPE.

The composite part is preferably designed on the one end thereof as a steel tube through which the care product can be conveyed. The steel tube is anchored in a stationary fashion in the brush body on the one end thereof. The flexible valve is arranged on the other end of the steel tube or composite part. As a result, there are no movable or abrading sealing surfaces between the tube and elastic valve as well as between the brush body and valve. Because of this type of mounting, there are no movable sealing surfaces at all that would, for example, abrade very rapidly under the impact of abrasive toothpaste. The valve appears through a sufficiently large hole in the brush disc so that there are no friction surfaces, either, and thus no abrasions can occur on the body of the flexible valve.

Only one movable surface (thrust surface 16) on which friction occurs is on the face side between the brush disc and metal tube. However, abrasions at this site, which mainly occurs on the plastic part of the brush disc, does not affect its function. The elastic valve 12 is preferably located within the metal tube 8 so that the outside cylinder surface of the metal tube can act as a contact surface for the brush disc. In a preferred embodiment, a metal sleeve 9 is pressed into the hole in the brush disc 3 so that metal rides on metal and also toothpaste causes as little abrasion as possible. Because metal parts can be manufactured very exactly, a very precise clearance fit can be obtained at low cost.

The composite part 6 consisting of two components is preferably pressed into the brush body 2 in the channel 7 through which the tooth care substance is fed. However, if the composite part loosens from the press fit, it will still be held in its position by the brush disc 3 and thus secured against falling out. By pressing the metal tube 8 into the hole in the brush body 2, metal tube 8 and channel 7 are sealed together. Additional parts such as O-rings for sealings are unnecessary.

On the face side, the brush disc is secured in the one direction by parallel thrust surfaces as stops in the direction of the brush body. These thrust surfaces have a multi-stage design. First, the surface 16 braces against the metal tube underneath the hole of the brush disc. If this surface shrinks, surface 17 and then surface 18 contact the corresponding opposite surfaces on the brush body 2. According to the invention, these surfaces wear down one after the other in sequence, starting from the smallest abrasion radius 16 up to the largest 18. This guarantees that a new brush experience the least frictional loss and thus performs best. As the brush ages, the frictional losses in the system increase only slightly. The brush disc is prevented from falling off in the other direction by a metal safety pin 10 incorporated into the brush body.

The invention is explained in further detail by means of an exemplary embodiment, which is represented in the figures.

FIG. 1 shows a replaceable replacement brush for an electric toothbrush with a brush body 2 and a movable brush disc 3 that is provided with cleaning elements 4 and 5 in a known manner.

Figure 2:
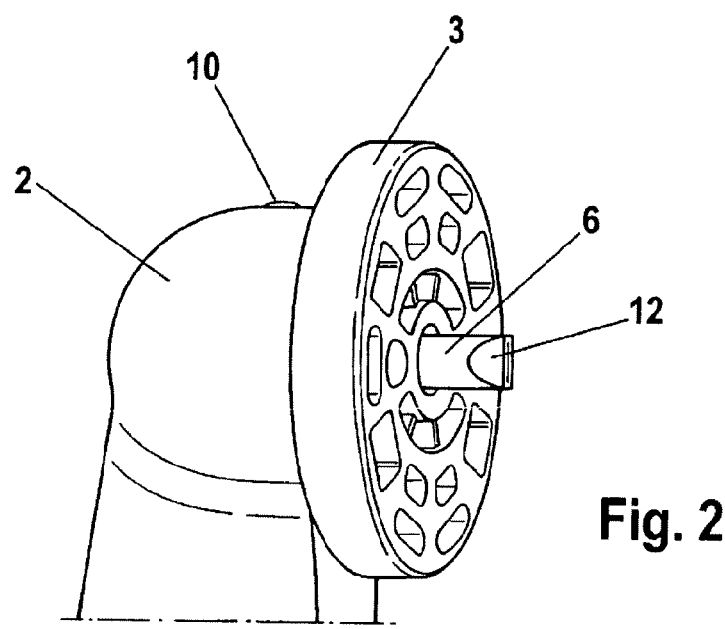

FIG. 2 shows a brush head with the brush body 2 onto which the brush disc 3 is mounted. In the middle of the disc is a hole through which a composite part 6, which is made of flexible material, dips and protrudes over the brush disc. An incorporated safety pin 10 secures the disc 3 against loosening.

Figure 3:
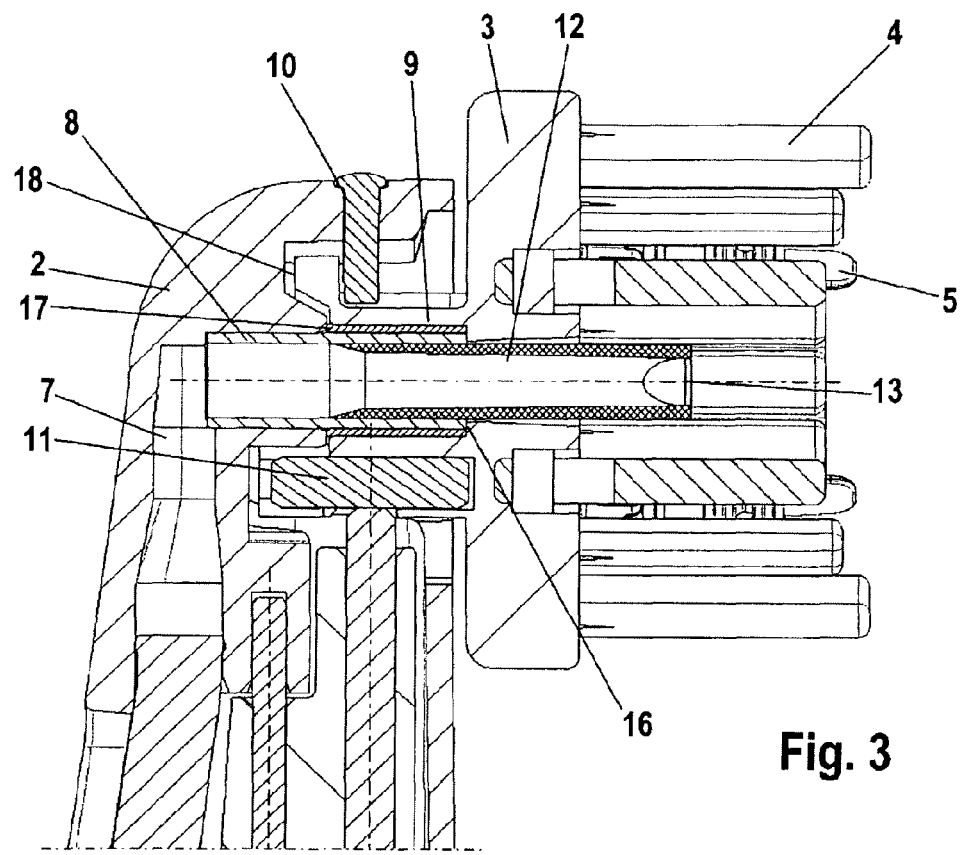

FIG. 3 shows a cross-section through a brush head. The care product is fed by the replacement brush into a channel 7. From there the care product is fed by a metal tube 8 into the flexible valve 12, from which it can leave through a slot 13.

The metal tube 8 is pressed into the brush body 2. The valve 12 passes through a hole in the brush disc 3 to which the bunch of bristles 4 and flexible element 5 are attached. The brush disc 3 is mounted on the brush body 2. The brush disc 3 is secured against loosening in an axial fashion by a safety pin 10. A metal sleeve 9, which is pressed into the hole of brush disc 3, acts as a contact surface for the rotation of the brush disc. The metal sleeve 9, together with the metal tube 8 of the valve, forms the mounting for brush disc 3. The axial thrust surface of brush disc 3 against brush body 2 with the smallest abrasion radius is surface 16; surface 17 is the next that comes into contact. If the brush disc has been incorporated into both surface 16 and surface 17, surface 18, with the largest abrasion radius will finally come into effect. A drive element 11 can shift the brush disc in a preferably oscillating and rotating movement.

Figure 4:
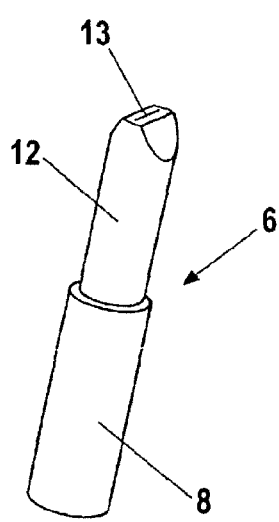

FIG. 4 shows the composite part 6, consisting of steel tube 8 and flexible valve 12, along with slot 13 for discharging the care product. The elasticity of the flexible material normally closes this slot 13 and only opens when pressure is applied from within. Thus, the valve acts as a check valve that only opens in one direction.

Figure 5:
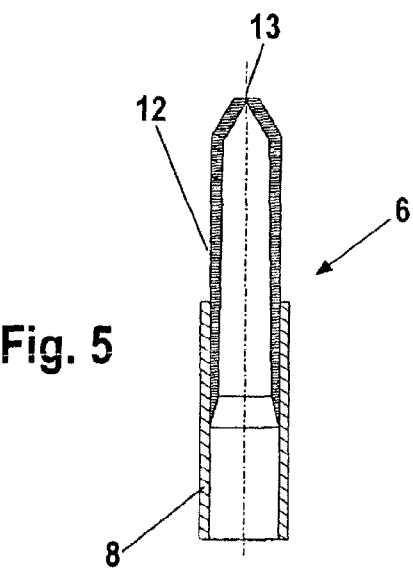

FIG. 5 shows the composite part 6 in a cross-section with steel tube 8, elastic valve 12 and slot 13.

All individual parts of the brush head are reliably attached to the brush body under all conceivable conditions of use. Small, loose parts in the mouth can not only cause choking but can also, under unfavorable circumstances, find their way to the lungs. Therefore, for safety reasons, it is absolutely necessary to guarantee that all parts are completely attached to the brush head. According to the invention, this is achieved for the discharge valve so that the bearing surface for the rotatable brush disc and the flexible discharge valve are manufactured as a composite part. With the construction described above, it is almost impossible for the valve to loosen in the mouth.

What is claimed is:

1. A brush head for a toothbrush comprising:
    a brush disc mounted in a rotable fashion on a brush body;
    a channel with an opening for the application of an oral care product, and a composite part including a rigid tube and an elongated elastic valve;
    wherein a portion of the valve is fixed to an inner part of the tube to serve as a rotational bearing for the brush disc.

2. The brush head according to claim 1, wherein the tube is made of metal.

3. The brush head according to claim 1, wherein the valve is designed as a slotted valve.

4. The brush head according to claim 1, wherein the valve is made of rubber and the tube is made of steel, and a vulcanization process firmly connects them to one another.

5. The brush head according to claim 1, wherein the brush disc has a radial bearing hole into which a sleeve is pressed.

* * * * *